United States Patent [19]
Kay

[11] Patent Number: 4,808,173
[45] Date of Patent: Feb. 28, 1989

[54] OSTOMY APPLIANCE COUPLING WITH VISCOELASTIC LINER

[75] Inventor: Paul O. Kay, Libertyville, Ill.

[73] Assignee: Hollister Incorporated, Libertyville, Ill.

[21] Appl. No.: 149,631

[22] Filed: Jan. 28, 1988

Related U.S. Application Data

[63] Continuation-in-part of Ser. No. 894,322, Aug. 7, 1986, abandoned.

[51] Int. Cl.[4] ............................................... A61F 5/44
[52] U.S. Cl. .................................... 604/339; 285/915
[58] Field of Search ............................ 604/332–345, 604/277; 285/291, 915; 277/152, 153, DIG. 6, 135; 156/293

[56] References Cited

U.S. PATENT DOCUMENTS

| | | | |
|---|---|---|---|
| 2,746,456 | 5/1956 | De Camillis | 604/342 |
| 3,557,790 | 1/1971 | Hauser | 604/342 |
| 3,897,781 | 8/1975 | Marsan | 604/338 |
| 4,530,525 | 7/1985 | Schneider | 604/341 |

FOREIGN PATENT DOCUMENTS 2387643 12/1978 France .............................. 604/344

Primary Examiner—John D. Yasko
Assistant Examiner—J. L. Kruter
Attorney, Agent, or Firm—Tilton, Fallon, Lungmus

[57] ABSTRACT

A coupling ring assembly for an ostomy appliance in which one of the rings has a generally radially-facing annular channel for receiving and detachably engaging a latching flange of the other of the rings, the channel having a deformable liner of viscoelastic polymeric material secured therein. In a preferred embodiment, the liner also has pressure-sensitive adhesive properties.

9 Claims, 2 Drawing Sheets

OSTOMY APPLIANCE COUPLING WITH VISCOELASTIC LINER

RELATED APPLICATION

This application is a continuation-in-part of my co-pending application No. 894,322, filed Aug. 7, 1986.

BACKGROUND AND SUMMARY

Co-pending co-owned U.S. Pat. No. 4,610,676 discloses an ostomy appliance coupling ring construction composed of a pair of relatively flat rings formed of polyethylene or other relatively soft, flexible plastic material. One of the rings has a tubular neck portion of limited axial extent terminating in an annular rim, the configuration defining a generally outwardly-facing channel that receives the annular collar or flange of the other ring when the two are coupled together. Contact between the two rings within the channel is responsible for producing an effective liquid-tight seal between the parts, and that seal is maintained despite the flexing and bending to which the rings are subjected in use because of a second zone of contact, well outboard from the sealing zone, that performs a primary latching function.

The basic purpose of the coupling ring assembly of the aforementioned patent, and of all other recent coupling ring assemblies for ostomy appliances, is to facilitate replacement of an ostomy pouch while at the same time permitting the adhesive faceplate to remain in position on the wearer's body. Thus, over a period of days, a number of pouches will be coupled to and uncoupled from a single faceplate coupling ring. Each time such coupling/uncoupling actions occur, there is a risk that the sealing surfaces of the rings might become scratched (as by a fingernail), nicked, or otherwise damaged. Any such damage, even a scratch too small to be readily observed by the naked eye, may be enough to provide a leakage pathway when the rings are joined together. The problem is compounded by the fact that such appliances are frequently worn by elderly or infirm patients who lack the minimal dexterity needed for easily coupling and uncoupling the rings and who may have difficulty manipulating such rings without damaging their sealing surfaces.

An important aspect of the present invention lies in the discovery that problems of leakage may be virtually eliminated, and other significant benefits may be obtained, if a viscoelastic polymeric liner is secured within the radially-facing channel of one of the rings. Particularly advantageous results are achieved if the viscoelastic liner, in addition to being deformable, also has controlled pressure-sensitive adhesive properties. Whether adhesive or not, the elastomeric liner deforms in response to unequal forces exerted by the flange of the other coupling ring when it is seated within the channel. Any voids between the two rings that might otherwise result in leakage or fluid bypass are effectively eliminated. The viscoelastic liner is also able to adjust itself to slight dimensional variations that may exist between successive pouch rings, thereby giving the user assurance that a single faceplate ring may be successively coupled to a multiplicity of pouch rings without risks of leakage.

Where the viscoelastic liner also has adhesive properties, it augments the security of attachment between the two rings as well as insuring against leakage. It is essential that the bond between the liner and the channel in which it is retained be greater than the adhesive attraction between the liner and the flange of the other ring so that, when the other ring is removed, the liner will remain within the channel. This may be achieved by forming the liner of a hot melt adhesive and then flowing that adhesive in a molten state into the channel where it solidifies or cures. Selective adherence of the liner to the channel-providing ring may also be controlled by selecting an appropriate formulation or surface treatment for the respective rings so that the surface of the other ring has less affinity for the adhesive than that of the channel-providing ring. Such treatments are well known in the art as disclosed, for example, in Park, W. R. R., Plastics Film Technology, pp. 154 et seq., (Van Nostrand Reinhold Company, 1969), and Satas, D., Handbook of Pressure Sensitive Adhesive Technology, 371 et seq., (Van Nostrand Reinhold Company, 1982).

Where the liner also has adhesive properties, it contributes in providing a coupling ring assembly that requires greater force to disassemble than to assemble. A user finds the rings may be easily slipped together into coupled relation. The substantially greater force required to separate them provides security against possibilities of unintentional separation of the parts.

Other features, advantages and objects of the invention will become apparent from the specification and drawings.

DRAWINGS

DETAILED DESCRIPTION OF PREFERRED EMBODIMENT

Figure 1:
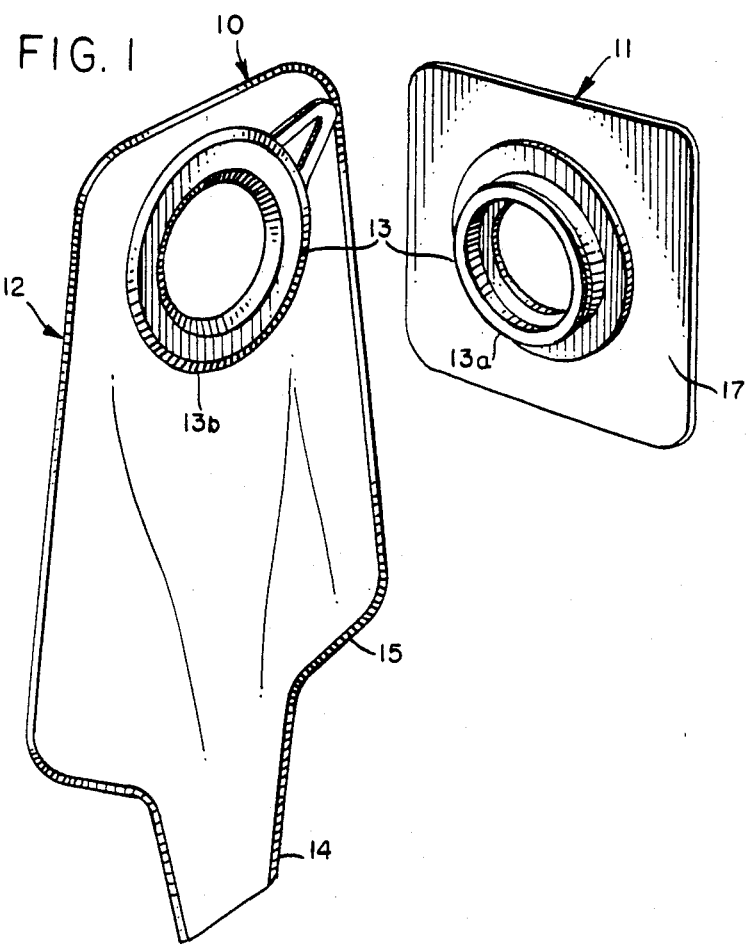
FIG. 1 is a perspective view of an ostomy appliance equipped with a coupling ring assembly of this invention, the ostomy bag and faceplate being shown in separated condition for clarity of illustration.

Referring to the drawings, the numeral 10 generally designates an ostomy appliance having a faceplate 11 and a bag or pouch 12. A two-piece coupling ring assembly 13 is provided for detachably coupling the faceplate and pouch, one element of the assembly being faceplate ring 13a and the other being pouch ring 13b.

Both the pouch and the faceplate may vary considerably in size, shape, and construction, all as well known in the art, and it is to be understood that coupling assembly 13 is not limited in its use to the particular pouch and faceplate constructions depicted in the drawings. For example, pouch 12 is shown to have an outlet 14 at its lower end, such outlet being intended to be closed by a suitable clamping device (not shown) such as the one disclosed in U.S. Pat. No. 3,523,534; however, the pouch may if desired be "non-drainable," in which case outlet 14 would be omitted. Typically, pouch 12 is designed to be relatively flat and is composed of two sheets or walls 12a and 12b of flexible thermoplastic film that are heat sealed together along their outer margins as indicated at 15 in FIG. 1.

Faceplate 11, in the particular form illustrated in the drawings, is constructed generally in accordance with the teachings of U.S. Pat. No. 4,213,458 and reference may be had to that patent for information on the details of construction. Faceplate 11 includes a highly flexible patch or panel 17 formed of gas-penetrable but water resistant microporous material. Various materials having such properties are known and may be used. In any case, the faceplate should be highly flexible so that it will conform readily to body contours and body movements, and be coated on its back or rear side with a medical-grade pressure-sensitive adhesive so that upon removal of backing sheet or sheets 18 the microporous adhesive-coated patch or panel 17 may be secured to the patient's skin in the peristomal region.

An attaching ring or collar 19 may be secured to the front face of the microporous patch 17 by heat sealing or by any other suitable means. The attaching ring must also be capable of being heat sealed or otherwise securely joined, either directly or indirectly, to ring 13a of the coupling ring assembly 13. In the construction depicted in the drawings, such connection is indirect to the extent that a web 23 of thin, flexible, and resilient thermoplastic material is interposed between faceplate ring 13a and the attaching ring 19 of faceplate 11, as generally disclosed in co-owned U.S. Pat. No. 4,419,100. Specifically, the inner margin of the annular web 23 is heat sealed at 20 to the faceplate 11 and its outer margin is heat sealed at 24 to faceplate ring 13a. The web gives rise to a floating relationship between the faceplate ring 13a and faceplate 11, promoting conformity of the faceplate to a wearer's body without resistance from the coupling rings and, in general, allowing limited movement of the faceplate ring in generally axial directions with respect to the faceplate. Such limited movement allows a user to insert his (her) fingers between the ring 13a and faceplate 11 to facilitate attachment and detachment of the coupling rings without causing discomfort. The web should be formed of a heat sealable, tough, and durable material that is also capable of functioning as a fluid and odor barrier. Low density polyethylene coextruded with a coextensive layer or core of polyvinylidene chloride, known under the designation Saranex, from Dow Chemical Company, Midland, Mich., has been found suitable but other materials having similar properties are available and may be used.

Figure 2:
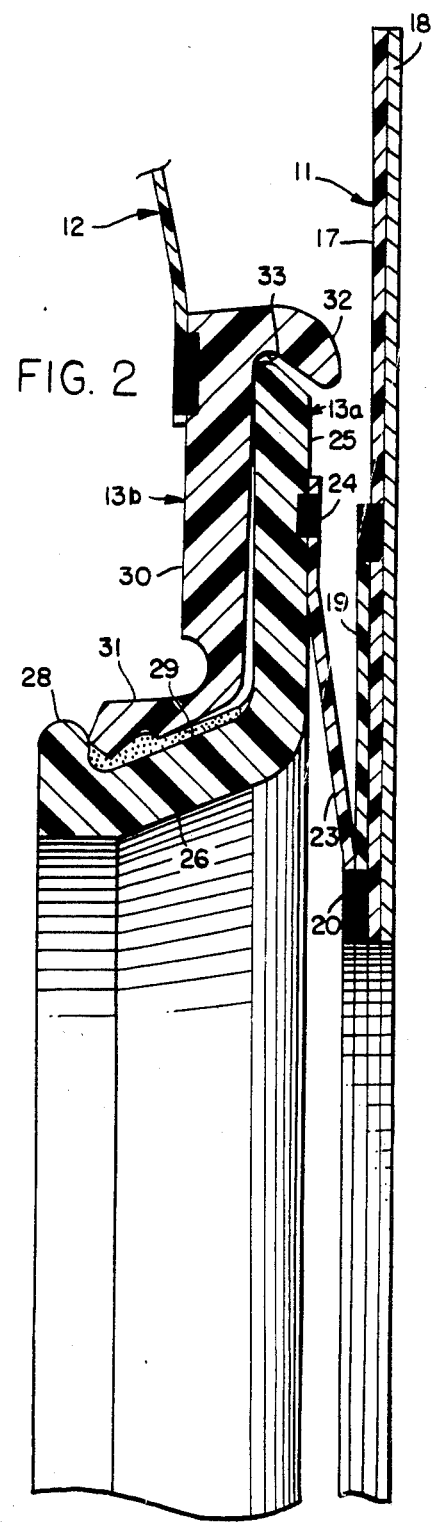
FIG. 2 is a somewhat enlarged schematic fragmentary sectional view showing the relationship of parts when the rings are coupled together.
Figure 4:
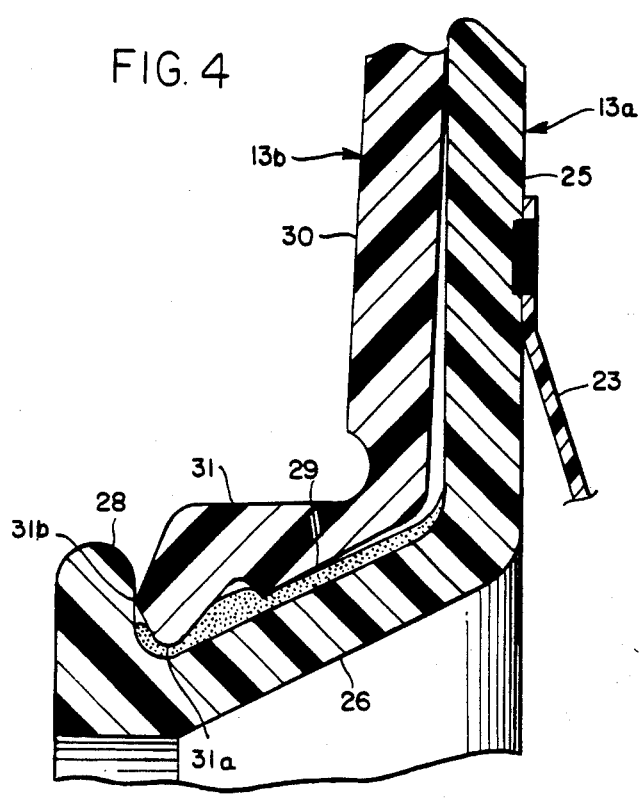
FIG. 4 is an enlarged sectional view similar to FIG. 3 but showing deformation of the liner when the flange of a pouch ring is received within the channel.

The coupling ring assembly, and particularly the structural relationship between faceplate ring 13a and pouch ring 13b, is illustrated most clearly in FIGS. 2 and 4. Ring 13a has an annular body portion 25 and an integral tubular neck portion 26. At its outer limits, the planar body portion 25 provides an annular latching shoulder 27 that is shown to be continuous although, if desired, the latching shoulder may be discontinuous or interrupted along its circumference.

The neck portion 26 of ring 13a tapers axially and forwardly away from planar body portion 25 and, at its front or distal end, has an annular and radially-outwardly projecting rim 28. The rim, neck portion, and body portion together define a radially-facing annular channel 26a. Within that radially outwardly-facing channel is a liner or layer 29 of viscoelastic polymeric sealant material.

Figure 3:
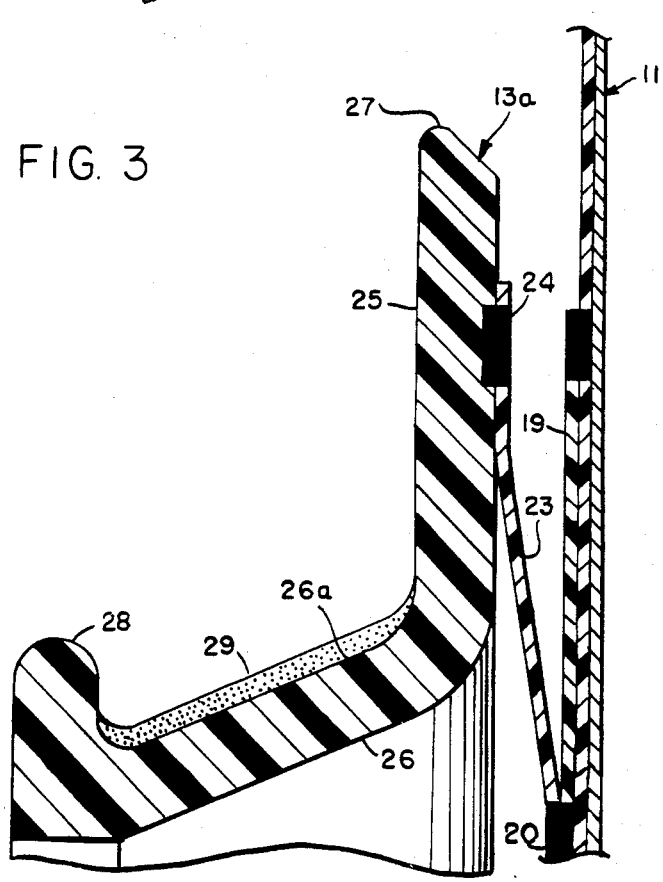
FIG. 3 is a still further enlarged schematic fragmentary sectional view of the faceplate ring with its viscoelastic sealant liner.

The liner 29 is readily deformable and, in an undisturbed state, assumes the condition shown in FIG. 3 of the drawings. In that state, it provides a substantially uniform coating or layer along the base of channel 26a. Since the liner is securely bonded to the neck portion 26 of the coupling ring 13a, it is not free to be displaced from the channel. However, the configuration it assumes within the channel may be substantially altered, as indicated in FIGS. 2 and 4.

The viscoelastic liner may be formed of any of a variety of materials having a combination of properties, in varying degrees, of deformability, recoverability, tackiness, and flow. Low durometer thermoplastic elastomers such as silicone rubber, polyurethane, or polybutene/polyisoprene may be used and may be applied by coating from a dispersion or solvent system, by mechanical transfer, or by any other suitable technique. Ideally, the viscoelastic liner is formed in place by flowing it into the channel in molten state. For that purpose, the melting temperature of the sealant liner material should not so far exceed the melting temperature of the thermoplastic material from which ring 13a is formed that the ring becomes deformed or damaged as the molten liner material solidifies, it being understood that a slight momentary softening of the surface of the ring by the molten sealant may be beneficial in producing an even more secure bond between the ring and the sealant liner. In view of the manner of its application, the liner material may be referred to generally as a "hot-melt sealant". Such hot melt sealants are well known and are ordinarily composed of thermoplastic elastomers blended with polyethylene or ethylene copolymers and, in many cases, tackifiers such as terpenoids or polyisobutylene.

Particularly effective results have been achieved where the viscoelastic sealant, in addition to being thermoplastic, deformable, and elastically recoverable, also has pressure-sensitive adhesive characteristics. Again, hot melt adhesives having such properties are known and any of a number of them may be used for this purpose. For example, one such material is available under the designation HM6515 from H. B. Fuller Company, St. Paul, Minn. Others are designated as 34-2881 from National Starch & Chemical Corporation, Bridgewater, N.J., and 84116 from Swift Adhesives Division, Reichhold Chemicals, Inc., Chicago, Ill. As well known in the art, hot-melt pressure-sensitive adhesives, when applied in a molten state to compatible surfaces, bond securely to such surfaces with forces that exceed the adhering forces that would exist if such adhesives were first cooled to solidifying temperatures (e.g., room temperature) before being brought into contact with such surfaces. While such pressuresensitive adhesive properties of hot-melt adhesives may contribute in promoting a more effective seal between the coupling rings (a function that is believed to be achieved largely by the sealant's deformability), they clearly result in a more secure connection between the parts. The hot melt material is applied in a molten state by flowing it into channel 26a to form a liner having a thickness within the range of approximately 0.01 to 0.05 of an inch.

The pouch coupling ring 13b is provided with a body portion 30 that extends in a plane normal to the central axis of that ring. A generally frusto conical collar portion or flange 31 tapers axially from the inner margin of the body portion 30, the general direction of taper of the flange being the same as that of the neck portion 26. The inner surface of the flange is provided with an annular projection 31a, such projection defining the smallest inside diameter of the flange for sealingly engaging the liner 29 along the outer surface 26 of ring 13b. At its distal or free end, the flange is provided with an axially-facing annular ridge 31b that normally abuts rim 28 when the parts are assembled as shown in FIGS. 2 and 4.

Along its outer perimeter, body portion 30 merges with an annular latching rib 32 which projects inwardly and axially in a direction opposite from that of flange 31 and which, along with the remainder of body portion 30, defines an outwardly and rearwardly facing recess 33 for detachably receiving and retaining the shoulder 27 of faceplate ring 13a. The rib 32 may be provided with rounded surfaces, as shown in FIG. 2, to facilitate latching engagement and disengagement of the two rings.

Excluding deformable sealant liner 29, coupling rings 13a and 13b are similar to those described in co-pending U.S. Pat. No. 4,610,676 and reference may be had to such patent for further details concerning the features, functions, and advantages of such ring construction. While rings 13a and 13b are believed to represent a particularly effective coupling ring arrangement for utilizing sealant liner 29, it is believed that numerous modifications and variations in ring structure might be made. Thus, especially where liner 29 has pressure-sensitive adhesive properties, it may be possible to omit entirely the rib 32 and its outboard latching function. Alternatively, the radially inwardly-facing surfaces defining recess 33 may also be lined with viscoelastic sealant material to convert the outer latching zone into a latching/sealing zone.

Figure 5:
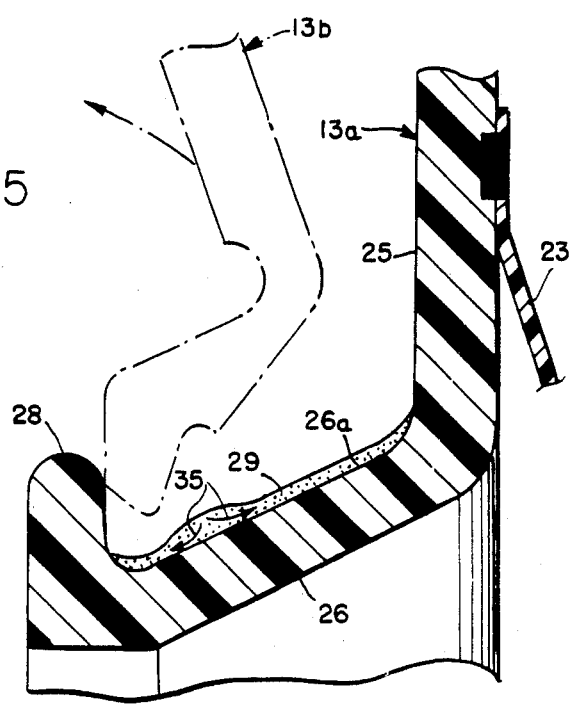
FIG. 5 is a fragmentary sectional view depicting the viscous flow or change in liner configuration as the forces exerted by the coupling ring flange are removed.

The important characteristic of the sealant liner 29 is graphically depicted in FIGS. 3-5. In an undisturbed state, the viscoelastic liner is generally of uniform thickness (FIG. 3) but it is readily deformed by forceful contact by flange 31 and particularly by its projection 31a (FIG. 4). By reason of such forceful contact, the viscoelastic material flows or is displaced circumferentially, radially, and axially to insure that no voids or gaps exist between the liner 29 and flange 31. The sealant liner or layer 29 and the rings 13a and 13b are so proportioned that some displacement of the liner must take place when the parts are fitted together. Upon separation of the parts, the memory characteristics of the viscoelastic material cause it to return at least partially in the direction of arrows 35 to its original undisturbed state (FIG. 5). Consequently, pouch rings 13b may be repeatedly coupled to and uncoupled from faceplate ring 13 with the viscoelastic liner being capable at each occasion of yieldably engaging the pouch ring and forming a fluid-tight seal therewith.

Where the liner has pressure-sensitive adhesive properties, rings 13a and 13b may be made even more flexible to conform with changes in body contour without risk that detachment of the rings might unintentionally occur. Thus, the resilient and flexible coupling rings, which may be formed of low-density polyethylene, may be made of flatter profile so that they do not protrude as far from the surface of the patient's body. Not only does such a construction make the product less noticeable, but the lower profile also allows the rings to conform more readily with changes demanded by body movements, thereby producing greater comfort for the patient and reducing the possibilities that the adhesive faceplate might pull away from the skin.

The use of a hot-melt sealant liner that also has pressure-sensitive adhesive properties may be valuable in achieving a more secure fluid-tight connection between other types of medical couplings, such as intravenous set couplings, where the forces required for separation of the parts should substantially exceed those required for their assembly and where it is imperative that fluid-tight (liquid and gas) connections be achieved.

EXAMPLE 1

The preferentially greater adhesion of a hot-melt pressure-sensitive sealant for a surface to which it is applied in a molten state, in comparison with its adhesion to a similar surface which it contacts in a solidified state, is illustrated by the following:

Linear ribbons or beads of hot-melt adhesive (adhesive 34-2881, National Starch & Chemical Corporation, Bridgewater, N.J.) were extruded by means of a conventional hot-melt adhesive gun set at 340° F. onto smooth planar surfaces of test slabs of polyethylene (Dow 779). The molten hot-melt sealant so applied to each slab was allowed to cool for approximately 3 minutes, at which time the smooth surface of a second slab, substantially identical to the first slab, was placed over the first slab in forceful contact with the solidified sealant.

Thereafter, the pairs of slabs were peeled apart following procedures generally in accordance with ASTM D903-49 as reapproved 1983. Since the test slabs of polyethylene were flexible (each having a thickness of approximately 1/16 of an inch), different peel angles could be utilized. For certain sample pairs, peeling forces were applied at 180° (i.e., in opposite directions) and for other pairs the peeling forces were 90° apart. In still other instances, no peeling forces were used but only shearing forces, involving no flexing of the slabs, were applied to the slab pairs. In all cases in which separation forces were applied to the pairs of slabs, the adhesive sealant remained with the first slab, that is, the slab to which it had been applied in molten form, and separated from the slab with which it had been brought into contact following solidification. The forces of separation in pounds of force for 9 such tests were found to be as follows:

| 90° Peel | 180° Peel | 180° Shear |
| --- | --- | --- |
| 34.6 | 21.0 | 89.5 |
| 16.6 | 7.0 | 74.9 |
| 11.8 | 15.7 | 91.9 |

EXAMPLE 2

Preferential adherence as indicated in Example 1 was also found to exist when pairs of coupling rings having constructions as generally depicted in FIGS. 1 through 5 were snapped together, allowed to remain in coupled condition at body temperature for extended periods, and then separated under controlled and force-measuring conditions.

The coupling rings of such sample pairs were formed of polyethylene (Dow 779 for faceplate ring 13a and Dow 722 for pouch ring 13b) with the viscoelastic liner 29 being formed of a hot-melt pressure-sensitive adhesive (hot-melt 34-2881, National Starch & Chemical Corporation, Bridgewater, N.J.) that was flowed in molten condition (over 300° F.) into the radially-facing channel 26a of faceplate ring 13a while that ring was rotated upon a support fixture. Following cooling and solidification of the sealant and removal of ring 13a from its support fixture, pairs of rings 13a and 13b were snapped together and allowed to remain in coupled condition at body temperature (98° F.) for about 16 hours. The rings were then uncoupled in accordance with a prescribed procedure, starting with the unlatching of an edge of rib 32 at a point along shoulder 27 and followed by pulling the unlatched edge of that rib away from the supported ring 13a in an inward direction at 60° relative to the planar body portion 25 of ring 13a, with the peak forces required to cause final separation of the rings (at the zone of viscoelastic sealant) being measured by an Instron force measuring machine. For rings of different stoma opening sizes (1, 1.5, 2 and 2.5 inches) the forces in pounds were as follows:

| 1"  | 1.5" | 2"   | 2.5" |
|-----|------|------|------|
| 5.7 | 3.8  | 7.2  | 6.0  |
| 7.9 | 5.6  | 10.0 | 6.0  |
|     | 6.4  | 7.5  | 7.5  |
|     | 6.1  |      |      |
|     | 7.5  |      |      |

In each case, the viscoelastic sealant liner 29 separated cleanly from pouch flange 13b and remained securely bonded to faceplate flange 13a. Similar tests were conducted using other commercially available viscoelastic hot-melt sealants (e.g., Henkel Technomelt 0763) with similar results.

While in the foregoing I have disclosed an embodiment of this invention in considerable detail for purposes of illustration, it will be understood by those skilled in the art that many of these details may be varied without departing from the spirit and scope of the invention.

I claim:

1. A coupling ring for an ostomy appliance, said ring being formed of flexible plastic material and defining an axially-extending opening therethrough for receiving a patient's stoma; said ring also having a generally radially-facing annular channel for receiving and detachably engaging an annular flange of a second coupling ring adapted to mate with said first-mentioned ring; and a deformable liner of viscoelastic polymeric material securely and sealingly bonded to said first-mentioned ring within said channel for making direct, shape-conforming, fluid-tight sealing contact with said flange when said first and second rings are coupled together; said viscoelastic material comprising a hot-melt sealant having pressure-sensitive adhesive properties; the strength of the bond between said viscoelastic liner and said first-mentioned ring exceeding the strength of adhesion of said liner to said second-mentioned ring.

2. The ring of claim 1 in which said annular channel faces radially outwardly.

3. The ring of claim 2 in which an adhesive faceplate is secured to said first-mentioned ring for adhesive attachment of said ring and faceplate to a patient's skin about a stoma.

4. The ring of claim 1 in which the thickness of said viscoelastic liner in an unstressed state falls within the range of about 0.010 to 0.050 inches.

5. The ring of claim 1 in which said first-mentioned ring is formed of low density polyethylene.

6. A coupling for detachably connecting an ostomy faceplate to an ostomy pouch; said coupling including first and second coupling rings formed of flexible and resilient thermoplastic material; said first ring having a generally radially-facing annular channel and said second ring having an annular flange removably received within said channel when said rings are coupled together; and a deformable liner of viscoelastic polymeric material securely and sealingly bonded to said first ring within said channel and disposed in direct, shape-conforming, fluid-tight sealing contact with said flange when said first and second rings are coupled together; said viscoelastic material being a hot-melt sealant having pressure-sensitive adhesive properties with the strength of the bond between said sealant and said first ring exceeding the strength of adhesion of said sealant to said second ring.

7. The coupling of claim 6 in which said annular channel of said first ring faces generally radially outwardly.

8. The coupling of claim 6 in which an adhesive faceplate is secured to said first ring for adhesive attachment to a patient's skin about a stoma.

9. The coupling of claim 6 in which the thickness of said viscoelastic liner in an undisturbed state is within the range of 0.010 to 0.050 inches.

* * * * *